United States Patent [19]

Birks et al.

[11] Patent Number: 4,947,045
[45] Date of Patent: Aug. 7, 1990

[54] SYSTEM FOR INSPECTING LARGE SIZE STRUCTURAL COMPONENTS

[75] Inventors: Albert S. Birks, Columbus, Ohio; James R. Skorpik, Kennewick, Wash.

[73] Assignee: Battelle Memorial Institute, Richland, Wash.

[21] Appl. No.: 294,785

[22] Filed: Jan. 9, 1989

[51] Int. Cl.$^5$ ............................................. G01N 23/02
[52] U.S. Cl. ............................. 250/360.1; 250/358.1
[58] Field of Search ............. 250/360.1, 363.01, 358.1; 378/59, 60

[56] References Cited

U.S. PATENT DOCUMENTS 3,775,612 11/1973 Foster et al. ........................... 378/59
4,283,628 8/1981 Kulekov et al. ....................... 378/60

FOREIGN PATENT DOCUMENTS 977468 11/1975 Canada .................................. 378/59
1816803 8/1969 Fed. Rep. of Germany ........ 378/60

OTHER PUBLICATIONS

"Faster Pipe-Weld Testing . . . ", Nucleonics, vol. 17, No. 1, Jan., 1959, p. 98.

Primary Examiner—Janice A. Howell
Assistant Examiner—Richard Hanig
Attorney, Agent, or Firm—Dellett, Smith-Hall and Bedell

[57] ABSTRACT

The present invention relates to a system for inspecting large scale structural components such as concrete walls or the like. The system includes a mobile gamma radiation source and a mobile gamma radiation detector. The source and detector are constructed and arranged for simultaneous movement along parallel paths in alignment with one another on opposite sides of a structural component being inspected. A control system provides signals which coordinate the movements of the source and detector and receives and records the radiation level data developed by the detector as a function of source and detector positions. The radiation level data is then analyzed to identify areas containing defects corresponding to unexpected variations in the radiation levels detected.

12 Claims, 4 Drawing Sheets

SYSTEM FOR INSPECTING LARGE SIZE STRUCTURAL COMPONENTS

This invention was made with government support under Subcontract No. RAHCO-SC-81-9553 awarded by R. A. Hanson Company, Inc. under Prime Contract No. F04704-81-C-0012 awarded by the U. S. Air Force. The government has certain rights in the invention.

BACKGROUND OF THE INVENTION

The invention relates to devices and methods for testing structural members and more specifically to systems for inspecting structural components by employing penetrating radiation to scan said components.

The testing of large scale structural members such as the concrete containment walls used in blast-proof buildings poses a difficult problem. These members are frequently of substantial size and are not ordinarily capable of being tested adequately in accordance with conventional inspection techniques because such techniques do not allow the integrity of the construction in their interior regions to be assessed. The type of inspection required might nevertheless be accomplished by taking core samples of components at different points. However, this would involve damaging the components themselves as part of the test procedure and is an expensive and time consuming undertaking for structural components of significant size.

It is, therefore, an object of the present invention to provide an improved inspection system which is operative on large scale structural components for identifying defects such as voids, areas of reduced thickness or density and honeycomb conditions.

It is another object of the present invention to provide an improved system for inspecting structural components which carries out its testing in a non-destructive fashion, i.e., without damaging the structural component under inspection, and with sufficient accuracy to reliably identify significant defects.

It is a further object of the present invention to provide an improved system for inspecting structural components which can rapidly and efficiently inspect components of substantial size but which is economical to construct and operate.

SUMMARY OF THE INVENTION

The present invention comprises a system for testing structural components such as concrete containment walls in order to assess the integrity of their construction and identify structural defects, for example voids, regions of reduced thickness and honeycomb conditions. This system includes a source module for supplying a beam of radiation of sufficient intensity to penetrate the structural component, and a detection module for detecting this radiation. Both the source module and detection module are constructed and arranged to be mobile in response to signals provided by a microprocessor-based control system. The control system is operative for coordinating the movements of the source and detection modules and recording the radiation level information developed by the detection module.

In a preferred embodiment, the source module includes a source material which provides gamma radiation such as cobalt 60, a collimator for directing the radiation in a beam and a projector for safely storing the radiation source material. These components are mounted on a wheeled cart that is conveyed by being pulled with a cable running to a stationary drive unit having a motor-driven drum around which the cable is wound. The detection module includes a scintillation detector secured to the end of a flexible metal hose. The detector is adapted for being drawn through one or more guide tubes having fixed positions by another stationary drive unit provided with a set of pinch rollers which push and pull the hose and attached detector through the guide tubes. Both the drive units for the source and detection modules include encoder wheels functioning to generate signals indicative of the positions of the source and detection modules, and these signals are supplied to the control system.

In operation, the source material carried on the cart and the detector attached to the hose are translated in substantial alignment with one another on parallel paths along opposite sides of the structural component to be inspected and particularly along one dimension of this component in accordance with control signals provided by the control system. The source module continuously projects a beam of penetrating gamma ray radiation through the structural component toward the detection module as the source material and detector travel along.

The detection module detects the levels of radiation transmitted through the structural component and supplies this data to the control system. The control system tabulates this data in conjunction with the information it receives about the positions of the source material and detector for a large number of sampling points and records these results on a permanent medium for analysis. The intensity levels for the transmitted radiation at the various sampling points along the structural component provide indications of integrity of the construction of the component at these points.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION

Figure 1:
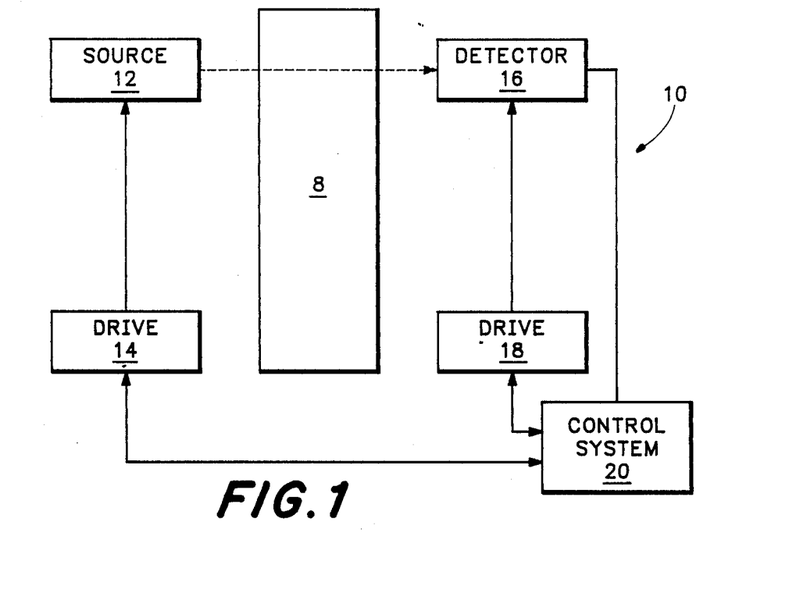
FIG. 1 is an overall functional block diagram of the inspection system which comprises the present invention.

Referring now to FIG. 1, the present invention comprises the inspection system 10 for assessing the integrity of the construction of structural component 8, such as a concrete containment wall. The system 10 includes a gamma ray radiation source module 12, a drive unit 14 for translating the source module 12, a gamma ray radiation detection module 16, a drive unit 18 for translating the detection module 16, and a microprocessor-based control system 20 for controlling and coordinating the movement of source and detection modules 12 and 16 by the drive units 14 and 18 and for recording the radiation intensity information developed by the detection module 16. In operation, the source module 12 and the detection module 16 are translated along opposite sides of a structural component 8 in a controlled manner such that substantial alignment is maintained. During this process readings are taken with respect to the radiation transmitted through the structural component 8 and these readings are recorded by the microprocessor system 20 as a function of the distances traveled by the source module 12 and the detection module 16 along the structural component.

Figures 2, 3:
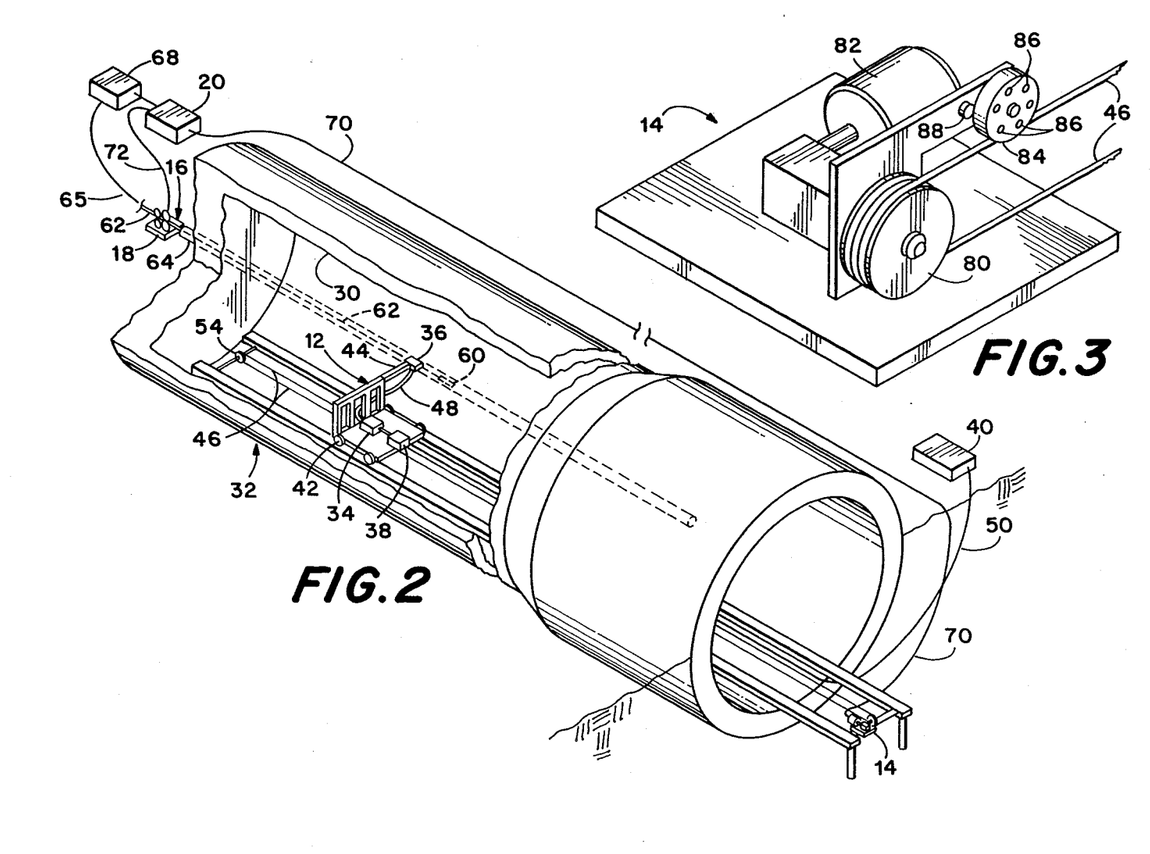
FIG. 2 is a diagrammatic perspective view of the mechanical components of the preferred embodiment of the present invention as installed in position for making an inspection.
FIG. 3 is a perspective side view of the cart drive unit component of the preferred embodiment of the present invention.

Referring now to FIG. 2, the preferred embodiment of the inspection system 10 is shown in position during the process of making an inspection of the containment wall 30 of a horizontally inclined concrete storage silo 32. The wall 30 is inspected by having the source module 12 and the detection module 16 travel down the silo 32 in an axial direction 35 along opposite sides of the wall 30 while being maintained in substantial radial alignment. In order to fully inspect the wall 30, a number of different inspection passes or scans would ordinarily be made with the source module 12 and the detection module 16 oriented at different radial angles relative to axis of the silo so that sets of data characterizing the entire wall 30 can be developed.

The source module 12 includes gamma ray radiation source material 28 initially located in source projector 34, a radiation collimator 36, a mechanical source drive 38 and a source controller 40. The gamma source projector 34, collimator 36 and source drive 38 are located on a movable cart 42 constructed of perforated steel tubing and mobile on a set of wheels for translation along the wall 30 inside the silo 32 when pulled by steel cable 46. Steel cable 46 is connected from one end of cart 42 to the cart drive unit 14 at the open end of the silo 32 and further extends from the cart drive unit 14 via a turnaround sleeve 54 located at the closed end of the silo 32 to the remaining end of the cart 42.

Projector 34 functions as a storage container for the gamma radiation source material 28 and suitably comprises a steel casing and a radiation shield of depleted uranium. Collimator 36 is connected to projector 34 by a flexible stainless steel guide tube 48 through which the source material travels, i.e., between the collimator 36 and projector 34. A safety switch may be installed in the guide tube 48 for indicating the position of the source material as either fully retracted into the projector 34 or exposed in the collimator 36. The collimator 36 functions to direct the radiation from the source material in a 20°×90° beam, and serves to help reduce backscatter. The collimator 36 is secured to the end of a movable arm 44 which may be fastened to the front of the cart 42 at various positions to provide different orientations for the collimator 36 and the radiation beam which it projects.

The source drive 38 contains drive motors which push the source material 28 through the guide tube 48 between the gamma source projector 34 and the collimator 36 via intermediate control cables. A cranking system is also provided which allows the operator to manually return the source material 28 from the collimator 36 to the projector 34 should mechanical or electrical failure take place in the system. Source controller 40 is remotely located with respect to the cart 42 at a stationary position outside the silo 32 and functions to regulate the operation of source drive 38 via control signals furnished over the lines 50 in response to input commands from a human operator.

The source material 28 suitably constitutes a radioactive isotope which produces gamma radiation pursuant to its natural processes of decay. This gamma radiation must be sufficiently intense and energetic to penetrate the structural member under inspection in detectable amounts. The preferred source material comprises Cobalt 60 which furnishes gamma radiation at the 1.17 MeV and 1.31 MeV energy levels, within proper range for penetrating concrete, and which has a 5.3 year half-life and therefore requires infrequent calibration of detection equipment.

Detection module 16 includes a scintillation detector 60, a braided and somewhat flexible stainless steel hose 62 suitably lined with teflon, one or more detector guide tubes 64, a detector drive unit 18 and a pulse processing system 68. The one or more guide tubes 64 are external to silo 32, i.e., normally on the opposite side of wall 30 from the radiation source material. The scintillation detector 60 is attached to the end of hose 62 and is adapted for being drawn back and forth down guide tubes 64 (suitably comprising metal conduit) one at a time via forces acting on hose 62. Hose 62 is connected to the detector drive unit 18 which pushes and pulls the hose 62 in a controlled manner in order to translate the detector 60 through the guide tube. If the entire wall is to be inspected, a plurality of the guide tubes 64 are extended axially along the outside of silo 32 in close proximity to the wall 30 at spaced-apart locations around the silo and substantially parallel to the silo axis so as to allow all of the sections of the wall 30 to be scanned. The pulse processing system 68 is electrically connected to the scintillation detector 60 through electrical lines 65 extending within hose 62, but is located in proximity to the microprocessor system 20 at a position remote from the detector 60.

The microprocessor control system is electrically connected to the cart drive unit 14 and the detector drive unit 18 via the lines 70 and 72 and to the pulse processing system 68 via line 74. The microprocessor system 20 receives information as to the location of the source and detection modules 12 and 16 and furnishes control signals regulating the operation of the cart drive unit 14 and detector drive unit 18 over the aforementioned lines 70 and 72. At the same time, the system 20 receives radiation level signal data from the pulse processing system 68 over line 74 and records the same as a function of the positions of cart 42 and detector 60.

Referring now to FIG. 3, cart drive unit 14 comprises a friction drum 80 mounted on the drive shaft of a DC gear motor 82. The cable 46 is wound around the drum 80 so that it can be driven by the motor 82. The cart drive unit 14 also includes an encoder wheel 84 engaging the surface of the cable 46 independently of the drum 80. A set of steel pins 86 are embedded along the outside edge of the encoder wheel 84 so as to pass by proximity switch 88 as the wheel rotates thereby generating electrical signals (pulses) indicative of the distance traveled by the cable 46 and the cart 42 attached thereto, specifically at one inch intervals. The proximity switch 88 is an inductive-type sensor having no moving parts and is non-contacting with respect to cable 46 and wheel 84.

Figure 4:
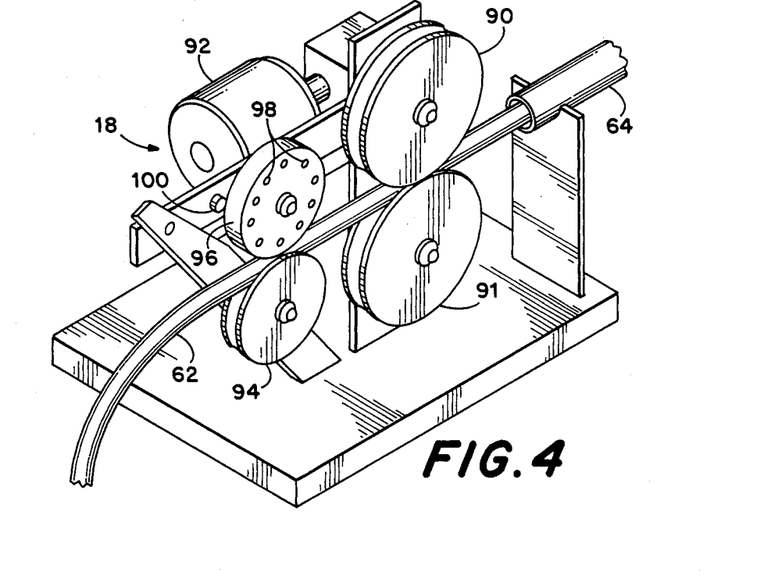
FIG. 4 is a perspective side view of the detector drive unit component of the preferred embodiment of the present invention.

Referring now to FIG. 4, detector drive unit 18 comprises a pair of pinch rollers 90 and 91 driven for counter-rotation by another DC gear motor 92. The drive unit 18 also includes an encoder wheel 96 which cooperates with guide wheel 94 and rides on the surface of the braided stainless steel hose 62. The hose 62 runs between the pinch rollers 90 and 91 so that it may be pushed and pulled through a guide tube 64 by the operation of the motor 92. A set of steel pins 98 are embedded along the outside edge of the encoder wheel 96 so as to pass by a proximity switch 100 as the wheel rotates thereby providing electrical signals (pulses) indicative of the distance traveled by the hose 62 and the scintillation detector 60 attached thereto in accordance with one inch intervals of movement. The proximity switch 100 is an inductive-type sensor which has no moving parts and is non-contacting with respect to hose 62 and wheel 96.

Figure 5:
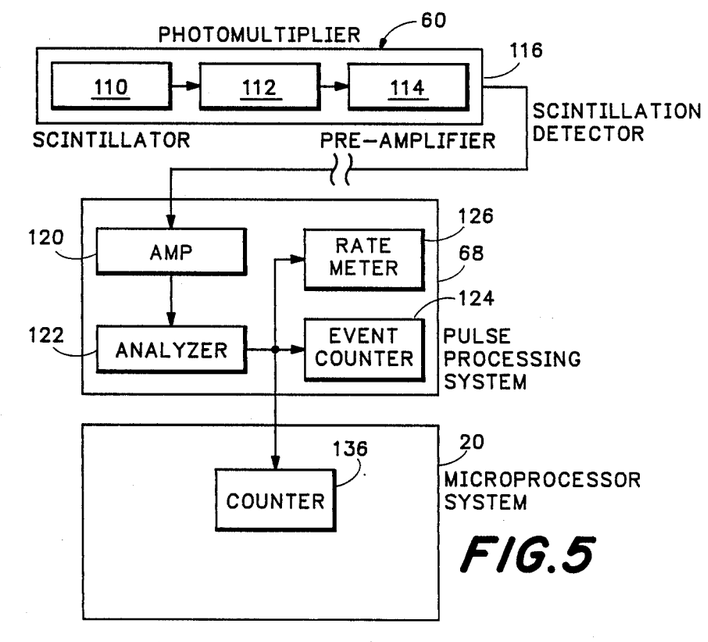
FIG. 5 is a diagrammatic view of the detection module component of the preferred embodiment of the present invention.

Referring now to FIG. 5, the scintillation detector 60 comprises scintillator crystal 110, a miniature photomultiplier tube 112 and a preamplifier 114. The scintillator crystal 110 constitutes a radiation sensitive crystal material such as sodium iodide (NaI) which is approximately 0.5 inch in diameter and 2 inches long. The scintillations which occur in this crystal are registered and amplified by the photomultiplier tube 112 (e.g. type R-647-01 or equivalent). The resulting electrical pulses are amplified by the pre-amplifier 114 for transmission to the pulse processing system 68. The scintillator crystal 110, photomultiplier tube 112 and preamplifier 114 are mounted on an aluminum housing secured within a circular stainless steel casing 116 which is designed to protect the components and to fit loosely within the guide tubes 64.

The pulse processing system 68 comprises a variable gain amplifier 120, a pulse analyzer 122, an event counter 124 and a pulse rate meter 126. The variable gain amplifier 120 has a maximum gain of 1200× and reduced step gains of 600×, 300×, 150× and 75×, and allows the detection equipment to be matched to the photomultiplier tube 112 and the preamplifier 114 so that the signal peaks of the pulses from the scintillation detector 60 occur at about the middle of the dynamic range of the analyzer 122. The radiation signal is supplied from the amplifier 120 to the pulse analyzer 122 where the pulses are subject to upper and lower thresholds set to establish a window corresponding to the energy level of the radiation (1.25 MeV±10 MeV for Co60) from source material and reject pulses at other energy levels representing radiation at levels outside the range of the source material (and especially secondary radiation due to scattering). The pulses which pass through the "window" established by the analyzer 122 are further amplified and clipped at the 10 volt level by the analyzer 122. The resulting signals are supplied to the event counter 124 and pulse rate meter 126 which provide visual indications to the operator of the radiation levels currently being sensed by the detector 60.

Figure 6:
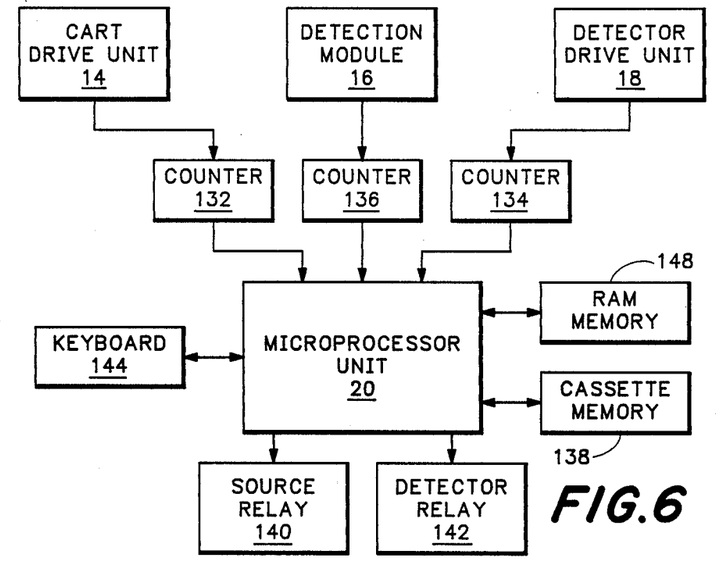
FIG. 6 is a functional block diagram of the basic electrical units comprising the control system component of the preferred embodiment of the present invention.

Referring now to FIG. 6, the electronic components which are associated with the system include microprocessor unit 20, three 16-bit counters 132, 134 and 136, a memory cassette recorder 138, a source drive relay 140, a detector drive relay 142, an input keyboard 144 and a RAM memory unit 148. The microprocessor unit is conventional in design and may comprise any of a number of readily available microprocessor chips such as the Intel 8085 microprocessor chip. The counters 132 and 134 are connected for receiving pulse signals from the proximity switches 88 and 100 of the drive units 14 and 18, respectively, the pulse signals being indicative of translation in one inch increments by the source material on the cart 42 and scintillation detector 60 attached to the hose 62. The tracking counters 132 and 134 record the number of pulses received, starting from initialization of the inspection system 10 at the time when the inspection process begins, thereby providing separate indications of the total distances traveled by the source module 12 and detection module 16 which can be compared to determine and maintain their alignment. The radiation level counter 136 is connected for receiving radiation pulse signals from the analyzer 122 in the pulse processing system 68 and continuously records the number of pulses received over successive intervals, suitably 80 milliseconds in duration. At the end of each such interval, the microprocessor unit 20 reads and stores the accumulated count value in RAM memory 148 and then reinitializes the counter 136. The source drive and detector drive relays 140 and 142 control the DC power supplied to the motors 82 and 92, thereby controlling the movement of the source material 28 on the cart 42 and detector 60 attached to the hose 62. The cassette recorder 138 provides a means for permanently recording the radiation levels sensed by the detection module 16 and the corresponding positions of the source material 28 and detector 60 in digital format so that this information is available for analysis. The keyboard 144 allows the operator to enter commands into the microprocessor 20, e.g. for starting the inspection process and initially configuring the inspection system 10.

Figure 7:
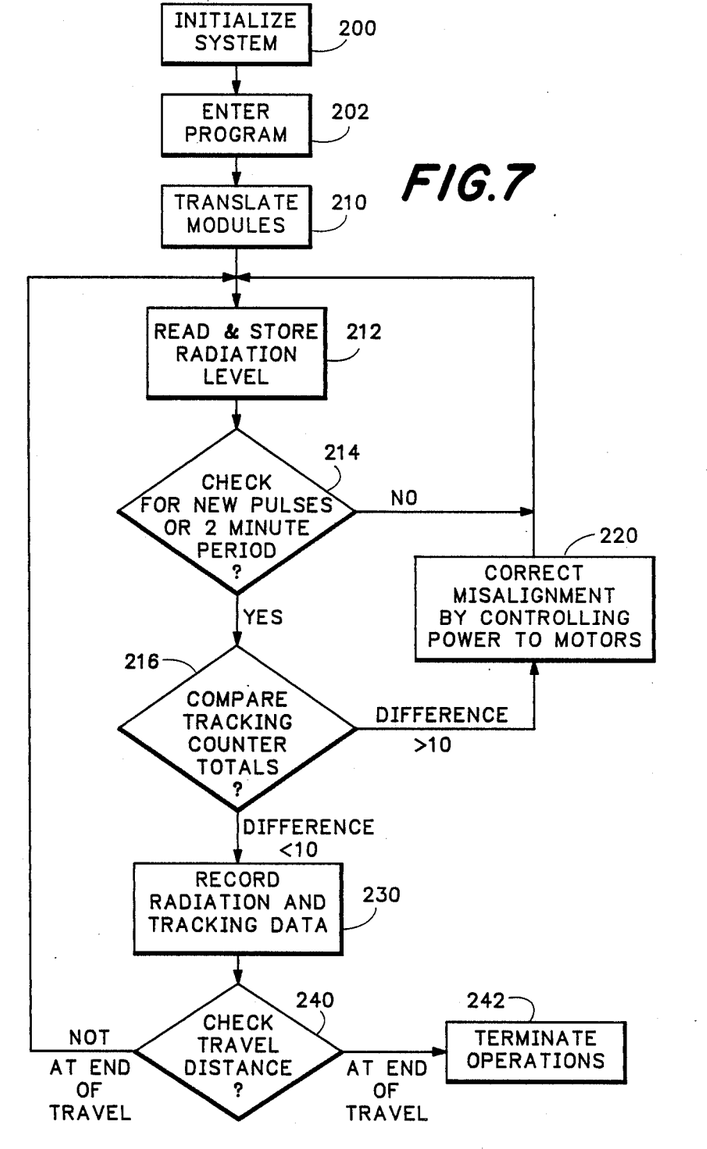
FIG. 7 is a flowchart of the overall method of operation of the inspection system which comprises the present invention.

Referring now to FIG. 7, the inspection system 10 operates in accordance with the steps shown, whereby the source material 28 conveyed on the cart 42, and the scintillation detector 60 attached to hose 62, are advanced together along a structural component such as the containment wall 30. Their alignment is preserved by the operation of the microprocessor 20 which also records the radiation levels experienced by the scintillation detector 60 as a function of the distances traveled by the cart 42 and hose 62. In step 200 the system 20 is initialized with, among other things, the counters 132 and 134 being set to zero and the cassette recorder 138 being loaded with a new cassette, rewound and otherwise prepared for data recordation. Additionally, the power supply levels to the DC motors 82 and 72 and to the photomultiplier tube 112 are set for system operation. With the power on, radiation readings are taken by the detection module 16 and the resulting pulses are registered by the counter 136. In step 202 the microprocessor system 20 is activated and the system software for conducting an inspection scan along a structural member is loaded. Execution of the inspection program is begun. In step 210, under control of the inspection program, the drive relays 140 and 142 are engaged and the cart drive unit 14 and detector drive unit 18 are supplied with power. As a result, the cart 42 (and radiation source material 28) and the hose 62 (and radiation detector 60) begin moving together along opposite sides of the structural component being inspected, such as the wall 30 of the silo 32 of FIG. 2, at a moderately slow rate, e.g. 10 ft/min. In accordance with step 212 the output of the counter 136 is read by the microprocessor unit on 80 millisecond intervals with the counter 136 being reset each time it is read. The counter output is temporarily stored in the RAM memory unit 148.

At step 214 the program checks to see if a pulse has been received from one of the proximity switches 88 and 100 or, alternatively, if a two second period of time has elapsed since the last set of data was permanently recorded on tape by the system. In either case, then the program proceeds to step 216 in which the alignment of the source module 12 and detection module 16 is verified. In order to ascertain the alignment of the modules, the outputs of the counters 132 and 134 are compared. If the difference between their count totals is greater than or equal to a number such as 10 which is sufficient for structural components having thicknesses of approximately 20 inches to indicate substantial misalignment, the program proceeds to step 220. Alternatively, if the difference between the count totals is less than 10, the program proceeds to step 230. In step 220 the power to the DC motor 82 or 92 of the module 12 or 16 having the highest count total is shut off through the action of the appropriate drive relay 140, 142 as controlled by the microprocessor unit until the value of difference between the count totals of the counters 132 and 134 reaches zero. The program then reverts to step 212, again reading and temporarily storing radiation data from the counter 136.

In step 230 the radiation count total currently accumulated in the counter 136, and tracking counter totals in the counters 132 and 134 for the sampling point corresponding to the current positions of source material 28 and detector 60, are permanently recorded in a correlated set on data memory tape maintained by the cassette recorder 148 for later analysis. When step 230 is completed, the program executes step 240 wherein the progress of travel by the source and detection modules 12 and 16 is checked by inspection of the current totals of the counters 132 and 134. If they are at the end of the inspection scan along the structural component, the program proceeds to step 242 whereby the power to the DC motors 82 and 92 is turned off and the inspection routine is terminated. Otherwise, step 212 is again entered and the procedures following thereafter are executed in order to acquire further data sets for additional points along the structural component being inspected.

The end result of one or more scans of a structural component is a compilation of radiation level readings for different points along the structural component. Unexpected variations in these radiation level readings provide reliable indications of problems relating to the integrity of the construction of the structural component and frequently identify structural defects at the points of variation. This effect can be explained from a mathematical viewpoint by virtue of the tendency of materials to absorb radiation and for radiation to penetrate through materials in accordance with exponential functions, whose exponents relate to the thickness of the material, and a constant equal to the attenuation coefficient of the material, as described in equation (1) below:

$$I_+ = I_o e^{-ut} \tag{1}$$

where:
t = thickness of material u = attenuation coefficient (approx. 0.282 per inch for concrete)
$I_o$ = incident radiation intensity
$I_+$ = transmitted radiation intensity (for a thickness t), It should be noted that the foregoing expression assumes a narrow beam of radiation is used and that negligible amounts of secondary radiation are produced due to scattering. Since the attenuation coefficient for gamma radiation in concrete is approximately 0.282, one inch of concrete will absorb approximately 25% of the radiation incident upon it. Since radiation level variations of ±5% or less can be easily detected, density variations and thickness variations or flaws can be readily identified using the present invention.

While a preferred embodiment of the present invention has been shown and described, it will be apparent to those skilled in the art that many changes and modifications may be made without departing from the invention in its broader aspects. For example, the radiation source does not have to be isotopic and may constitute another type of source of high energy photons such as an X-ray tube generating X-rays sufficiently penetrating with respect to the containment wall under examination. The appended claims are therefore intended to cover all such changes and modifications as fall within the true spirit and scope of the invention.

We claim:

1. A system for use in conducting nondestructive testing of containment walls for the structural defects, said system comprising:
    (a) a mobile radiation source constructed and arranged for movement along one side of a containment wall;
    (b) a mobile radiation detector constructed and arranged for movement along the other side of said wall on a path substantially parallel to said mobile source; and
    (c) a control unit operative for coordinating the movement of said source and detector so that said source and said detector are advanced together and maintained in substantial alignment with one another, and for recording readings taken by said detector as a function of distance traveled by said source and detector along said wall.

2. The system of claim 1 wherein said source includes:
    a gamma source projector for safely storing a gamma ray source material; and
    a collimator for use in positioning said source material and directing radiation therefrom toward said detector.

3. The system of claim 1 wherein said radiation source includes:
    a drive assembly comprising a cart for supporting said source which is attached to a cable wound around a motor-driven drum for taking up said cable and moving said source in response to control signals from said control unit; and
    means for tracking the movement of said radiation source and providing signals indicative thereof to said control unit.

4. A method for detecting construction defects such as voids, reduced wall thickness and honeycomb conditions in structural components having extended dimensions such as containment walls, said method comprising the steps of:

projecting a beam of gamma radiation from a radiation source into a structural component at one position along one side of said component;

detecting the level of gamma radiation emitted from said structural component with a radiation detector on the other side of said component at a position in substantial alignment with said source position;

translating said radiation source along one of the dimensions of said structural component; and translating said radiation detector along said one dimension of said structural component;

wherein said radiation source and said radiation detector are advanced together for substantially simultaneous movement in a coordinated manner so as to maintain relative positioning of said source and detector and scan possible defects in said structural component.

5. The method of claim 4 the step of:
wherein translation of said source and detector is coordinated by comparing data corresponding to the locations of said source and said detector and adjusting the positions of said source and detector when said data indicate a misalignment between said source and said detector.

6. The method of claim 4 wherein said step of translating said radiation source is performed by directing the movements of a wheeled cart conveying said source.

7. An apparatus for assessing the integrity of the construction of a structural component having one or more extended dimensions, said apparatus comprising:
   (a) a radiation source adapted for projecting a beam of gamma radiation into said structural component;
   (b) means for translating said radiation source along one side of said structural component;
   (c) a radiation detector adapted for sensing the level of radiation passing through said structural component;
   (d) means for translating said radiation detector along the other side of said structural component substantially concurrently and in parallel with said source; and
   (e) means for controlling and coordinating the translation of said source and said detector so that relative positioning in substantial juxtaposition is maintain on opposite sides of said structural component.

8. The apparatus of claim 7 wherein said means for translating said radiation source includes a drive assembly comprising a wheeled cart attached to a cable wound around a motor-driven drum for effecting movement of said source in response to control signals from said means for controlling and coordinating the translation of said source and detector.

9. The apparatus of claim 7 wherein said means for translating said radiation detector includes a drive unit having pinch rollers for pushing and pulling on a flexible hose attached to said detector in order to move said detector in response to control signals from said means for controlling and coordinating the translation of said source and detector.

10. A system for use in conducting non-destructive testing of containment walls for structural defects, said system comprising:
   (a) a mobile radiation source constructed and arranged for movement along one side of a containment wall;
   (b) a mobile radiation detector constructed and arranged for movement along the other side of said wall on a path substantially parallel to said mobile source; and
   (c) a control unit operative for coordinating the movement of said source and detector so that said source and said detector are maintained in substantial alignment with one another, and for recording readings taken by said detector as a function of distance traveled by said source and detector along said wall;

wherein said detector includes:
   a scintillation detector for detecting gamma radiation, said detector being attached to a flexible hose;
   a guide tube installed along said containment wall for use in positioning said detector and guiding its movement;
   a drive unit having roller means for pushing and pulling said detector through said guide tube by acting on said hose in response to control signals from said control unit; and
   means for tracking the movement of said detector and providing signals indicative thereof to said control unit.

11. A method for detecting construction defects such as voids, reduced wall thickness and honeycomb conditions in structural components having extended dimensions such as containment walls, said method comprising the steps of:

projecting a beam of gamma radiation from a radiation source into a structural component at one position along one side of said component;

detecting the level of gamma radiation emitted from said structural component with a radiation detector on the other side of said component at a position in substantial alignment with said source position;

translating said radiation source along one of the dimensions of said structural component; and translating said radiation detector along said one dimension of said structural component in coordination with said radiation source so as to maintain relative positioning of said source and detector;

wherein said step of translating said radiation detector is performed by drawing said detector down a guide tube.

12. An apparatus for assessing the integrity of the construction of a structural component having one or more extended dimensions, said apparatus comprising:
   (a) a radiation source adapted for projecting a beam of gamma radiation into said structural component;
   (b) means for translating said radiation source along one side of said structural component;
   (c) a radiation detector adapted for sensing the level of radiation passing through said structural component;
   (d) means for translating said radiation detector along the other side of said structural component substantially in parallel with said source; and
   (e) means for controlling and coordinating the translation of said source and said detector so that their relative positioning is maintained on opposite sides of said structural component;

wherein said means for controlling and coordinating the translation of said source and detector includes a microprocessor means which is adapted for receiving signal data indicative of locations of said source and detector, for comparing said signal data and furnishing control signals which adjust the positioning of said source and said detector to said means for translating said source and said detector when the source and detector are not in relative alignment, and which is adapted for receiving radiation level data from said detector and recording the last mentioned data as a function of the positions of said source and said detector.

* * * * *

UNITED STATES PATENT AND TRADEMARK OFFICE
CERTIFICATE OF CORRECTION

PATENT NO. : 4,947,045

DATED : August 7, 1990

INVENTOR(S) : Albert S. Birks; James R. Skorpik

It is certified that error appears in the above-identified patent and that said Letters Patent is hereby corrected as shown below:

Cover page, Attorney, Agent, or Firm-- "Dellett, Smith-Hall and Bedell" should read --Dellett, Smith-Hill and Bedell--.

Column 8, line 30, after "walls for" delete "the".

Column 9, line 17, after "claim 4" delete "the step of:".

Signed and Sealed this

Twenty-fourth Day of December, 1991

Attest:

HARRY F. MANBECK, JR.

*Attesting Officer*  *Commissioner of Patents and Trademarks*